US009739605B2

(12) United States Patent
Jeong et al.

(10) Patent No.: US 9,739,605 B2
(45) Date of Patent: *Aug. 22, 2017

(54) SHAPE MEASUREMENT APPARATUS AND METHOD

(71) Applicant: KOH YOUNG TECHNOLOGY INC., Seoul (KR)

(72) Inventors: Joong-Ki Jeong, Seoul (KR); Min-Young Kim, Seoul (KR); Seung-Jun Lee, Seoul (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/002,784

(22) Filed: Jan. 21, 2016

(65) Prior Publication Data
US 2016/0153772 A1 Jun. 2, 2016

Related U.S. Application Data

(63) Continuation of application No. 12/784,707, filed on May 21, 2010, now Pat. No. 9,275,292.

(30) Foreign Application Priority Data

May 21, 2009 (KR) .................. 10-2009-0044423
Jan. 26, 2010 (KR) .................. 10-2010-0007025

(51) Int. Cl.
*H04N 9/47* (2006.01)
*H04N 7/18* (2006.01)
(Continued)

(52) U.S. Cl.
CPC ........ *G01B 11/254* (2013.01); *G01B 11/2513* (2013.01); *G01B 11/2531* (2013.01); *G06K 9/036* (2013.01); *G01N 2021/95638* (2013.01)

(58) Field of Classification Search
CPC ..... G01B 11/24; G01B 11/25; G01B 11/2531; G01B 11/2527
(Continued)

(56) References Cited

U.S. PATENT DOCUMENTS 5,135,308 A * 8/1992 Kuchel ................. G06T 7/0057
250/237 G
5,166,811 A * 11/1992 Nagano .................. H04N 3/155
348/257
(Continued)

*Primary Examiner* — Jeremaiah C Hallenbeck-Huber
(74) *Attorney, Agent, or Firm* — Kile Park Reed & Houtteman PLLC

(57) ABSTRACT

A shape measurement apparatus includes a work stage supporting a target substrate, a pattern-projecting section including a light source, a grating part partially transmitting and blocking light generated by the light source to generate a grating image and a projecting lens part making the grating image on a measurement target of the target substrate, an image-capturing section capturing the grating image reflected by the measurement target of the target substrate, and a control section controlling the work stage, the pattern-projecting section and the image-capturing section, calculating a reliability index of the grating image and phases of the grating image, which is corresponding to the measurement target, and inspecting the measurement target by using the reliability index and the phases. Thus, the accuracy of measurement may be enhanced.

17 Claims, 10 Drawing Sheets

(51) Int. Cl.
*G01B 11/25* (2006.01)
*G06K 9/03* (2006.01)
*G01N 21/956* (2006.01)

(58) Field of Classification Search
USPC .......................................................... 348/136
See application file for complete search history.

(56) References Cited

U.S. PATENT DOCUMENTS

| | | | | |
|---|---|---|---|---|
| 6,650,443 | B1* | 11/2003 | Izumi | H01L 27/148 |
| | | | | 250/208.1 |
| 6,823,080 | B2* | 11/2004 | Iijima | G06T 7/0065 |
| | | | | 348/42 |
| 2005/0046865 | A1* | 3/2005 | Brock | G01B 9/02057 |
| | | | | 356/495 |
| 2006/0077398 | A1* | 4/2006 | Cantin | G01B 11/25 |
| | | | | 356/512 |
| 2006/0109482 | A1* | 5/2006 | Duval | G01B 11/0608 |
| | | | | 356/605 |
| 2006/0158664 | A1* | 7/2006 | Koh | G01B 11/25 |
| | | | | 356/604 |
| 2007/0146683 | A1* | 6/2007 | Ohtomo | G01C 15/002 |
| | | | | 356/4.01 |
| 2007/0177159 | A1* | 8/2007 | Kim | G01B 11/2531 |
| | | | | 356/601 |
| 2007/0223805 | A1* | 9/2007 | Jeon | G01B 11/2527 |
| | | | | 382/154 |
| 2007/0296979 | A1* | 12/2007 | Morimoto | G01B 11/2545 |
| | | | | 356/609 |
| 2010/0268069 | A1* | 10/2010 | Liang | G06T 7/521 |
| | | | | 600/425 |

* cited by examiner

SHAPE MEASUREMENT APPARATUS AND METHOD

CROSS REFERENCE TO RELATED APPLICATION

This application is a continuation of U.S. patent application Ser. No. 12/784,707, filed on May 21, 2010 (currently pending), the disclosure of which is herein incorporated by reference in its entirety. The U.S. patent application Ser. No. 12/784,707 claims priority to and the benefit of Korean Patent Application Nos. 10-2009-0044423 filed on May 21, 2009, and 10-2010-0007025 filed on Jan. 26, 2010, the entire contents of which are incorporated herein by reference.

BACKGROUND OF THE INVENTION

Field of the Invention

Exemplary embodiments of the present invention relate to a shape measurement apparatus and a shape measurement method. More particularly, exemplary embodiments of the present invention relate to a shape measurement apparatus and a shape measurement method capable of enhancing accuracy of measurement.

Discussion of the Background

Electronic devices have been developed to have relatively lighter weight and smaller size. Therefore, possibility of defects in these electronic devices increases and apparatus for inspecting the defects is under development and improvement.

Recently, the technique for inspecting a three-dimensional shape becomes effective in various technical fields. In the technique for inspecting a three-dimensional shape, a coordinate measurement machine (CMM), which detects three-dimensional shape by a contacting method, was used. However, non-contact method for inspecting a three-dimensional shape by using optical theories has been under development.

Meadows and Takasaki developed shadow Moire method which is the representative non-contact method for inspecting a three-dimensional shape in 1970. However, the shadow Moire method has a problem that a grating for measurement should be larger than a measurement target in size. In order to solve the above problem, Yoshino developed the projection Moire technique. Additionally, Kujawinska applied the phase shifting method which is used for analysis of optical coherence to Moire technique for inspecting three-dimensional shape so that the measurement resolution is enhanced and the limitation of Moire pattern is removed.

These techniques for measuring three-dimensional shape may be used for inspection of a printed circuit board, and tries for enhancing accuracy are performed.

SUMMARY OF THE INVENTION

Exemplary embodiments of the present invention provide a shape measurement apparatus capable of measuring a two-dimensional shape together with a three-dimensional shape, and enhancing accuracy of measurement.

Exemplary embodiments of the present invention also provide a shape measurement method capable of measuring a two-dimensional shape together with a three-dimensional shape, and enhancing accuracy of measurement.

Exemplary embodiments of the present invention also provide a method of measuring a three dimensional shape capable of accurately measuring a three dimensional shape of a measurement target in total areas.

Additional features of the invention will be set forth in the description which follows, and in part will be apparent from the description, or may be learned by practice of the invention.

An exemplary embodiment of the present invention discloses a shape measurement apparatus. The shape measurement apparatus includes a work stage supporting a target substrate, a pattern-projecting section including a light source, a grating part transmitting and blocking light generated by the light source to generate a grating image and a projecting lens part making the grating image on a measurement target of the target substrate, an image-capturing section capturing the grating image reflected by the measurement target of the target substrate, and a control section controlling the work stage, the pattern-projecting section and the image-capturing section, calculating a reliability index of the grating image and phases of the grating image, which is corresponding to the measurement target, and inspecting the measurement target by using the reliability index and the phases.

The shape measurement apparatus may inspect a surface of a pad through the reliability index when the pad is the measurement target. The pad may be to be electrically connected to an external device. The reliability index may be at least one of an intensity, a visibility and a signal to noise ratio. The control section may determine the pad is bad, when the reliability index is out of a setup value. The shape measurement apparatus may further include a subsidiary light source for inspecting the measurement target of the target substrate. The control section may determine that the pad is bad when light generated by the subsidiary light source is reflected by the pad and captured by the image-capturing section to form a two-dimensional image, and the pad is determined as bad in the two-dimensional image, even though the reliability index shows that the pad is good.

Another exemplary embodiment of the present invention discloses a shape measurement method. The shape measurement method includes acquiring a grating image reflected by a measurement target, while shifting the grating image for specific times, acquiring a reliability index including at least one of an intensity, a visibility and a signal to noise ratio of the grating image by using the grating image, and determining a pad for being electrically connected to an external device is good when the reliability index is within a setup value, and bad when the reliability index is out of the setup value, in case that the pad is the measurement target.

Still another exemplary embodiment of the present invention discloses a method of measuring a three dimensional shape. The method includes illuminating grating pattern lights in a plurality of directions onto a measurement target while changing each of the grating pattern lights by N times and detecting the grating pattern lights reflected by the measurement target, to acquire N pattern images of the measurement target with respect to each direction, extracting a phase $\{P_i(x,y)\}$ and a brightness $\{A_i(x,y)\}$ with respect to each direction corresponding to each position $\{i(x,y)\}$ in an X-Y coordinate system from the pattern images, extracting a height weight $\{W_i(x,y)\}$ with respect to each direction by using a weight function employing the brightness as a parameter, and calculating a weight height $\{W_i(x,y) \cdot H_i(x,y)\}$ with respect to each direction by using a height based on the phase with respect to each direction and the height weight, and summing weight heights, to produce a height $\{\Sigma W_i(x,y) \cdot H_i(x,y) / \Sigma W_i(x,y)\}$ at each position.

The brightness may correspond to an average brightness that is obtained by averaging the detected grating pattern lights.

The weight function may further employ at least one of a visibility and an SNR (signal-to-noise ratio) with respect to each direction extracted from the pattern images with respect to each direction as parameters.

The weight function may further employ a measurement scope ($\lambda$) corresponding to a grating pitch of each grating pattern light extracted from the pattern images with respect to each direction as a parameter. The measurement scope may have at least two values according to the grating pattern lights.

The weight function may decrease the height weight, as the average brightness increases or decreases from a predetermined value. The predetermined value may be a mid value of the average brightness.

The weight function may increase the height weight, as the visibility or the SNR increases.

The weight function may decrease the height weight, as the measurement scope increases.

Extracting the height weight with respect to each direction may include dividing the pattern images into a shadow area, a saturation area and a non-saturation area. The shadow area corresponds to an area, in which the average brightness is below a minimum brightness and the visibility or the SNR is below a minimum reference value, the saturation area corresponds to an area, in which the average brightness is more than a maximum brightness and the visibility or the SNR is below the minimum reference value, and the non-saturation area corresponds to a remaining area except the shadow area and the saturation area. The weight function may be regarded as '0' to obtain the height weight in the shadow area and the saturation area. The weight function corresponding to the non-saturation area may decrease the height weight, as the average brightness increases or decreases from a mid value of the average brightness, may increase the height weight as the visibility or the SNR increases, and may decrease the height weight as the measurement scope increases.

Sum of the height weights may be equal to 1 $\{\Sigma W_i(x,y)=1\}$.

Still another exemplary embodiment of the present invention discloses a method of measuring a three dimensional shape. The method includes illuminating grating pattern lights in a plurality of directions onto a measurement target while changing each of the grating pattern lights by N times and detecting the grating pattern lights reflected by the measurement target, to acquire N pattern images of the measurement target with respect to each direction, extracting a phase $\{P_i(x,y)\}$ and a visibility $\{V_i(x,y)\}$ with respect to each direction corresponding to each position $\{i(x,y)\}$ in an X-Y coordinate system from the pattern images, extracting a height weight $\{W_i(x,y)\}$ with respect to each direction by using a weight function employing the visibility as a parameter, and calculating a weight height $\{W_i(x,y)\cdot H_i(x,y)\}$ with respect to each direction by multiplying a height based on the phase by the height weight, and summing weight heights, to produce a height $\{\Sigma W_i(x,y)\cdot H_i(x,y)/\Sigma W_i(x,y)\}$ at each position.

According to the present invention, two-dimensional shape image may be obtained by using three-dimensional data measured, so that additional data for two-dimensional shape image may not be required.

Furthermore, when two-dimensional shape image and three-dimensional shape image, both of which are measured, are used together, defects of PCB may be effectively inspected.

Furthermore, when luminance of additional two-dimensional images used, accuracy of inspection may be enhanced.

In addition, average brightness, visibility or SNR, and measurement scope are extracted from the pattern images photographed in each direction, and height weight is determined according to the extracted result, to thereby more accurately measure a height at each position of measurement target in total areas including a shadow area and a saturation area.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
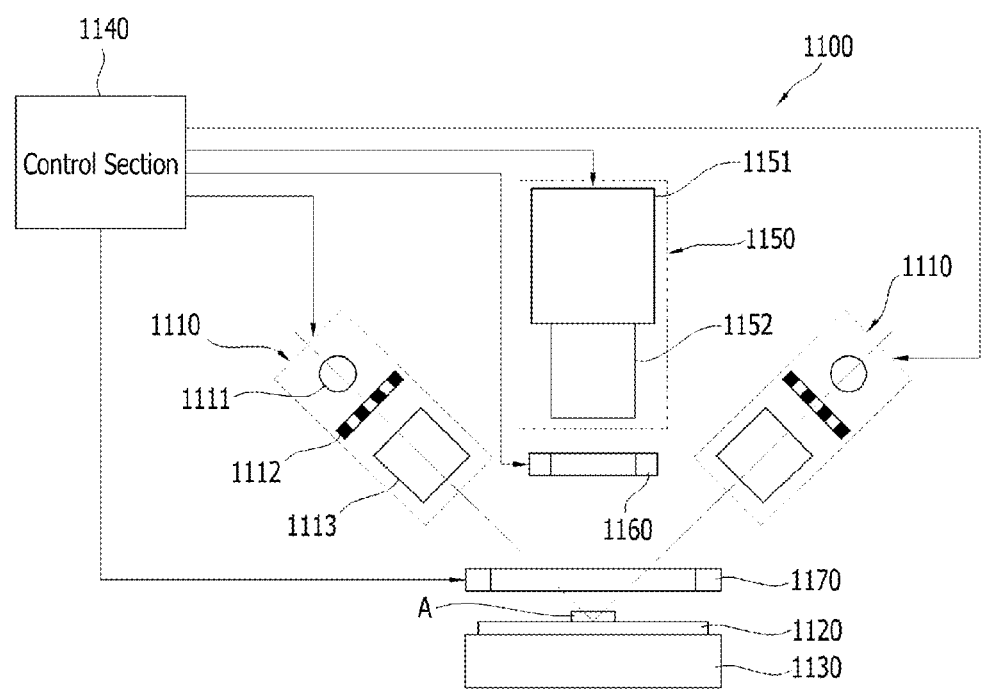
FIG. 1 is a schematic side view illustrating a shape measurement apparatus according to an exemplary embodiment of the present invention.

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments of the invention are described herein with reference to cross-sectional illustrations that are schematic illustrations of idealized example embodiments (and intermediate structures) of the present invention. As such, variations from the shapes of the illustrations as a result, for example, of manufacturing techniques and/or tolerances, are to be expected. Thus, example embodiments of the present invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, exemplary embodiments of the present invention will be described in detail with reference to the accompanying drawings.

FIG. 1 is a schematic side view illustrating a shape measurement apparatus according to an exemplary embodiment of the present invention.

Referring to FIG. 1, a shape measurement apparatus 1100 according to an exemplary embodiment of the present invention includes a work stage 1130, a pattern-projecting section 1110, an image-capturing section 1150 and a control section 1140. Additionally, the shape measurement apparatus 1100 may further include a first subsidiary light source 1160 and a second subsidiary light source 1170.

The work stage 1130 support a target substrate 1120 on which a measurement target A is disposed. Furthermore, the work stage 1130 transports the measurement target A along at least one of an x-axis direction and a y-axis direction. When the work stage 1130 is controlled to transport the target substrate 1120 to a proper position by the control section 1140, the first subsidiary light source 1160 and the second subsidiary light source 1170 may radiate a light toward the measurement target A of the target substrate 1120 to set up a total measuring regions of the target substrate 1120 by using, for example, a identification mark of the target substrate 1120.

The pattern-projecting section 1110 projecting a grating image toward the measurement target A. The shape measurement apparatus 1100 may include a plurality of the pattern-projecting sections 1110 disposed such that the plurality of pattern-projecting sections 1110 project grating images toward the target substrate 1120 with a specific angle with respect to a normal line of the target substrate 1120. Furthermore, the plurality of pattern-projecting sections 1110 may be disposed symmetric with respect to the normal line. Each of the pattern-projecting sections 1110 includes a light source 1111, a grating part 1112 and a projecting lens part 1113. For example, two the pattern-projecting sections 1110 may be disposed symmetrically with respect to the measurement target A.

The light source 1111 radiates light toward the measurement target A.

The grating part 1112 makes a grating image by using the light generated by the light source 1111. The grating part 1112 includes a light-blocking region (not shown) and a light-transmitting region (not shown). The light-blocking region blocks a portion of the light generated by the light source 1111, and the light-transmitting region transmits other portion of the light. The grating part 1112 may be formed in various types. For example, the grating part 1112 may be formed by a glass plate on which a grating with a light-blocking region and a light-transmitting region is patterned. Alternatively, a liquid crystal display panel may be used as the grating part 1112.

When the glass plate on which the grating with the light-blocking region and the light-transmitting region is employed as the grating part 1112, the shape measurement apparatus 1100 further includes an actuator (not shown) for minutely transporting the grating part 1112. When a liquid crystal display panel is employed as the grating part 1112, a grating pattern may be displayed by the liquid crystal display panel, so that the shape measurement apparatus 1100 does not need the actuator.

The projecting lens part 1113 makes a grating image of the grating part 1112 on the measurement target A of the target substrate 1120. The projecting lens part 1113 may includes, for example, a plurality of lenses, the grating part 1112 to focus the grating image to be displayed on the measurement target A on the target substrate 1120.

The image-capturing section 1150 receives the grating image reflected by the measurement target A of the target substrate 1120. The image-capturing section 1150 includes, for example, a camera 1151 and a capturing lens part 1152. The grating image reflected by the measurement target A passes through the capturing lens part 1152 to be captured by the camera 1151.

The control section 1140 controls the work stage 1130, the pattern-projecting section 1110 and the image-capturing section 1150, calculates a reliability index of the grating image captured by the image-capturing section 1150 and phases of the measurement target A, and processes the grating image captured by the image-capturing section 1150 to measure a two-dimensional shape and a three-dimensional shape. The process for measuring the two-dimensional shape and the three-dimensional shape, which is performed by the control section 1140, will be explained later in detail.

The control section 1140 inspects the measurement target by using the phase and the reliability index. In detail, the phase may be used for measuring the three-dimensional shape of the measurement target A, and the reliability index may be used for determining good or bad regarding the measurement target. For example, at least one of a signal intensity, a visibility and an SNR (Signal to Noise Ratio) may be used for the reliability index. The signal intensity may be explained referring to Expression 14 and Expression 15, the visibility may be explained referring to Expression 16 or Expression 17, and the SNR means a ratio of or difference between a periodic function generated during the N-bucket algorithm process of filtering images captured by the image-capturing section 1150 and a real signal. In more detail, the SNR is (visibility*D in Expression 1)/temporal noise D.

When the reliability index is out of a setup value, the control section 1140 determines the measurement target A as a bad one.

For example, the control section 1140 determines that the measurement target is bad, when the difference between the visibility γ of a specific region of the shape image obtained through Expression 16 or Expression 17 and the visibility γ of peripheral region is out of the range of the setup value.

Furthermore, one of the first subsidiary light source 1160 and the second subsidiary light source 1170 may be used for measuring two-dimension shape. In more detail, one of the first subsidiary light source 1160 and the second subsidiary light source 1170 radiates light toward the measurement target A of the target substrate 1120, and reflected light is captured by the camera 1151 of the image-capturing section 1150 to generate two-dimensional shape image.

Even when difference of the reliability index is within the setup value, the control section 1140 may determine that the measurement target A is bad when the luminance difference between the specific region of the two-dimensional shape image and the peripheral region of the two-dimensional shape image is out of another setup value. Furthermore, the control section 1140 may determine that the measurement target A is bad when the luminance of a specific region of the measurement target A is out of another setup value.

For example, even when the difference between the visibility γ of a specific region obtained through Expression 16 or Expression 17 and the visibility γ of a peripheral region is within the setup value, the control section 1140 determines that the measurement target A is bad when luminance difference or intensity difference between the specific region and the peripheral region of the two-dimensional image obtained through the first subsidiary light source 1160 or the second subsidiary light source 1170 is out of another setup value.

The control section 1140 inspects the two-dimensional shape and the three-dimensional shape of a region of interest (ROI) in fields of view (FOV) in sequence.

Figure 2:
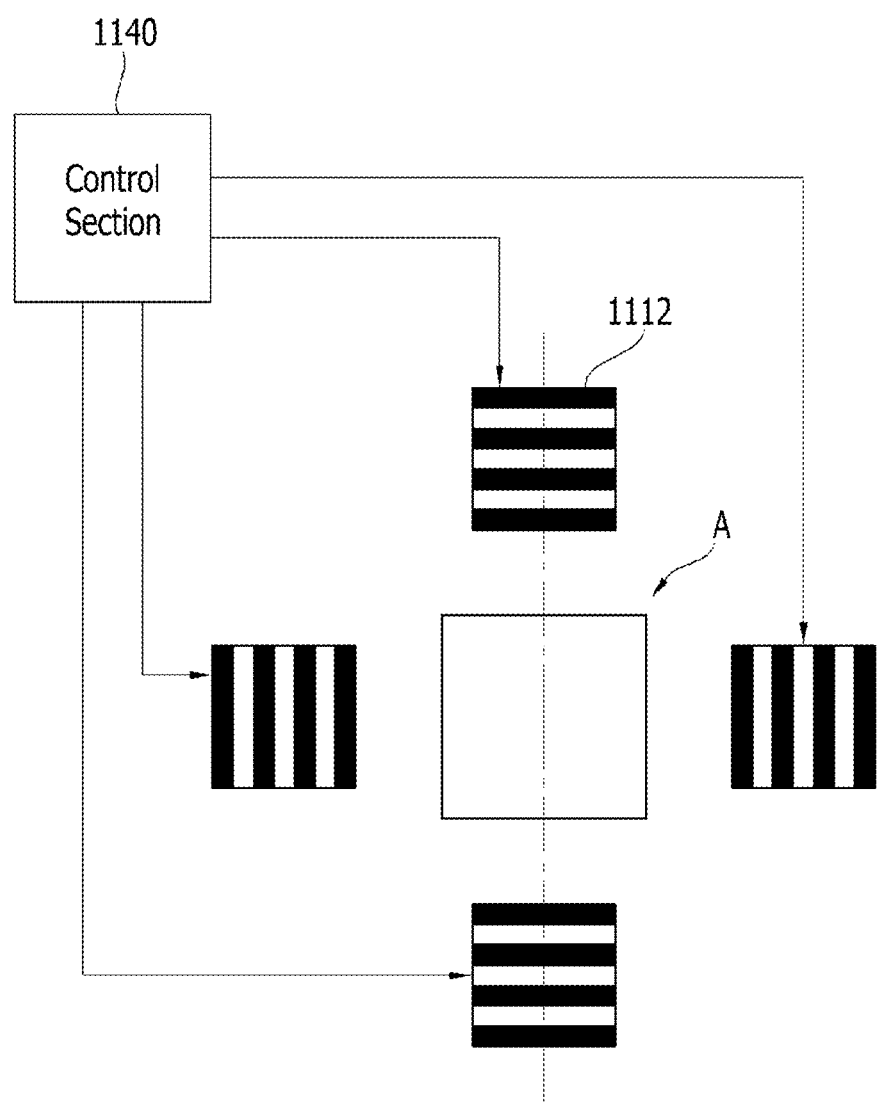
FIG. 2 is a schematic top view illustrating a shape measurement apparatus according to another exemplary embodiment of the present invention.

FIG. 2 is a schematic top view illustrating a shape measurement apparatus according to another exemplary embodiment of the present invention. The shape measurement apparatus according to the present embodiment is substantially same except for the pattern-projecting section of the shape measurement apparatus 1100 in FIG. 1. Therefore, same reference numerals will be used for the same elements and any further explanation will be omitted.

Referring to FIG. 2, the shape measurement apparatus according to the present embodiment includes a plurality of pattern-projecting sections 1110, each of which has a grating part 1112. The plurality of pattern-projecting sections 1110 is arranged at apexes of a polygon. In FIG. 2, four pattern-projecting sections 1110 are arranged at apexes of a square. However, the plurality of pattern-projecting sections 1110 may be arranged at apexes of hexagon, octagon, etc.

When the grating image is captured only at one side, exact three-dimensional shape may be obtained since the measurement target A is a protrusion so that the grating image may be arrive at the other side. Therefore, the grating image may be captured at both sides opposite to each other in order to obtain the exact three-dimensional shape.

For example, when the measurement target A has rectangular shape, the control section 1140 may turn on two pattern-projecting sections 1110 disposed opposite to each other. When the shape of the measurement target A, which is grasped by the control section 1140, is complex, the control section 1140 may turn on more than two pattern-projecting sections 1110.

Figure 3:
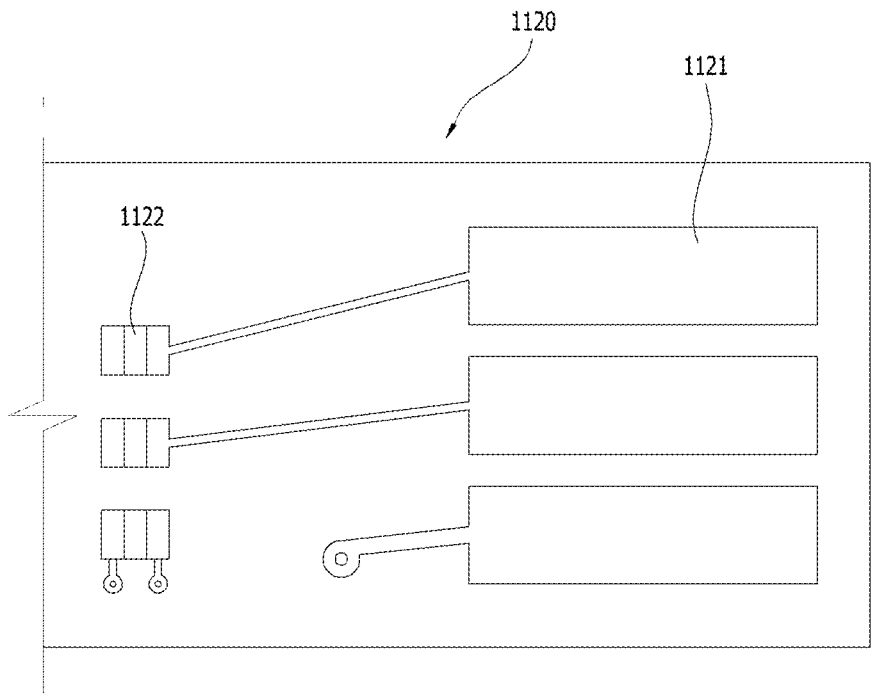
FIG. 3 is a top view illustrating a target substrate in FIG. 1.

FIG. 3 is a top view illustrating a target substrate in FIG. 1.

Referring to FIG. 3, the target substrate 1120 such as a printed circuit board (PCB) includes, for example, a pad region 1121 (or fan out region) and a device-mounting region 1122.

The pad region 1121 is a region in which a pad for electrical connecting is formed, and the device-mounting region 1122 is a region on which a device is mounted.

A device is mounted on the device-mounting region 1122 through solder paste. When the shape or the amount of the solder paste is not properly controlled, the device may be electrically connected with other devices to induce malfunction. Therefore, in order to check that the shape or the amount of the solder paste is property controlled, the shape and the height of the solder paste is measured to obtain three-dimensional shape of the solder paste.

Furthermore, the pad region 1121 should be checked for preventing electrical short with other pad region. In this case, two-dimensional shape obtained through Expression 14 or Expression 15 may be used for checking electrical short between the pad regions.

Additionally, the pad region 1121 should have flat surface. When the pad region 1121 is scratched, the pad region may induce a bad connection with a device. Therefore, the surface inspection of the pad region 1121 is very important.

For the surface inspection, the reliability index of the pad region 1121 is inspected. When the reliability index of a specific region is out of the setup value, the pad region 1121 is determined to be bad. Even when the reliability index of the specific region is within the setup value, a luminance difference of a specific region and a peripheral region in a two dimensional image obtained by using one of the first subsidiary light source 1160 and the second subsidiary light source 1170 in FIG. 1 is out of another setup value, the pad is determined to be bad since the pad has a scratch.

The pad region 1121 is a flat metal surface, so that the amount of light reflected by the pad region 1121 and captured by the camera 1151 of the image-capturing section 1150 in FIG. 1 may be saturated. Therefore, a shifted phase value may be measured. However the reliability index may be measured. Therefore, the pad region 1121 may be inspected by using the reliability index even when the amount of the light reflected by the pad region 1121 is saturated. Furthermore, the reliability index of each pattern-projecting section 1110 may be used as a weight value for the height measured by the each pattern-projecting section 1110.

Hereinbefore, the shape measurement apparatuses according to the present embodiments are explained. The shape measurement method according to the present embodiment is substantially the same as that of the shape measurement apparatus. That is, According to shape measurement method of the present invention, grating images reflected by a measurement target are obtained while shifting a grating, several times. Then, the reliability index of the grating images is obtained. When the reliability index is within the setup value, the measurement target is determined to be good, and when the reliability index is out of the setup value, the measurement target is determined to be bad. Furthermore, two-dimensional shape image of the measurement target may be obtained, and even when the reliability index of the pad is within the setup value, the pad may be determined to be bad when a luminance difference between a specific region and a peripheral region of the two-dimensional shape image is out of a specific value.

Figure 4:
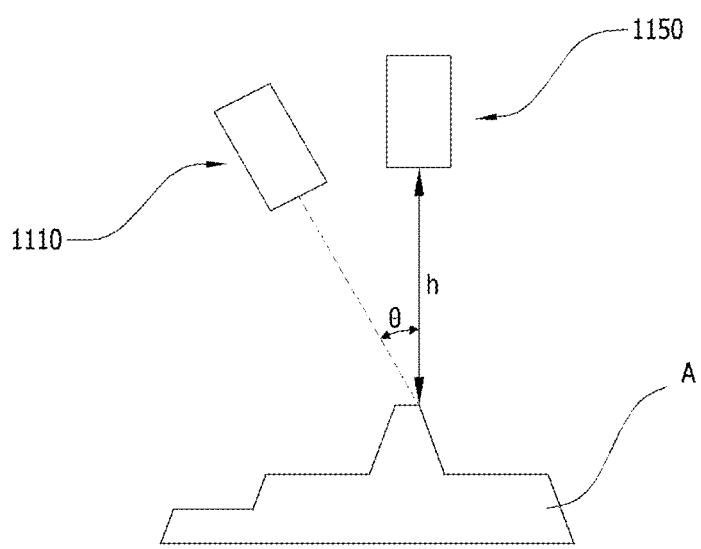
FIG. 4 is a diagram showing the shape measurement apparatus measuring a three-dimensional image.

FIG. 4 is a diagram showing the shape measurement apparatus measuring a three-dimensional image.

The grating image is radiated onto the target substrate 1120 in FIG. 1. Then, intensity I of images reflected by the target substrate 1120 and captured by the image-capturing section 1150 is expressed as the following Expression 1 corresponding to Moire equation.

$$I = D\left[1 + \gamma\cos\left(\frac{2\pi h}{\Lambda}\right)\right] \quad \text{Expression 1}$$

wherein I is intensity captured by the image-capturing section 1150, D is signal intensity (or a function of DC light intensity (or light source intensity) and reflectivity), $\gamma$ is visibility (a function of reflectivity and period of grating), $\Lambda$ is Moire equivalence period (a function of magnification, the period of grating and radiation angle $\theta$).

In Expression 1 intensity I is a function of height h, so that height h may be obtained by using intensity I.

When the phase of grating is shifted and reflected image is captured by the image-capturing section 1150 in FIG. 1, Expression 1 may be expressed as Expression 2.

$$I_k = D\left[1 + \gamma\cos\left(\frac{2\pi h}{\Lambda} + \delta_k\right)\right] \quad \text{Expression 2}$$

where $\delta k$ is phase shift, and $2\pi h/\Lambda$ corresponds to a phase $\Phi$ corresponding to the measurement target.

In order to obtain height h by using Expression 2, at least three phase shifts are required.

For example, when three phase shifts are applied (3-bucket algorithm), the height h may be obtained as follows. In Expression 2, zero radian is applied as $\delta 1$ to obtain I1, and then Expression 2 is expressed as following Expression 3.

$$I_1 = D\left[1 + \gamma\cos\left(\frac{2\pi h}{\Lambda}\right)\right] \quad \text{Expression 3}$$

In Expression 2, $2\pi/3$ radian is applied as $\delta 2$ to obtain I2, and then Expression 2 is expressed as following Expression 4.

$$I_2 = D\left[1 + \gamma\cos\left(\frac{2\pi h}{\Lambda} + \frac{2\pi}{3}\right)\right] \quad \text{Expression 4}$$

$$= D\left[1 - \gamma\left(\cos\left(\frac{2\pi h}{\Lambda}\right)\left(\frac{1}{2}\right) + \sin\left(\frac{2\pi h}{\Lambda}\right)\left(\frac{\sqrt{3}}{2}\right)\right)\right]$$

In Expression 2, $4\pi/3$ radian is applied as $\delta 3$ to obtain I3, and then Expression 2 is expressed as following Expression 5.

$$I_3 = D\left[1 + \gamma\cos\left(\frac{2\pi h}{\Lambda} + \frac{4\pi}{3}\right)\right] = \quad \text{Expression 5}$$

$$D\left[1 - \gamma\left(\cos\left(\frac{2\pi h}{\Lambda}\right)\left(\frac{-1}{2}\right) - \sin\left(\frac{2\pi h}{\Lambda}\right)\left(\frac{\sqrt{3}}{2}\right)\right)\right]$$

By using Expression 3, Expression 4 and Expression 5, following Expression 6 is obtained.

$$\frac{(I_3 - I_2)}{2I_1 - I_3 - I_2} = \tan\left(\frac{2\pi h}{\Lambda}\right) \quad \text{Expression 6}$$

By using Expression 6, the height h may be obtained as following Expression 7.

$$h = \frac{\Lambda}{2\pi}\tan^{-1}\left[\frac{\sqrt{3}\,(I_3 - I_2)}{2I_1 - I_3 - I_2}\right] \quad \text{Expression 7}$$

For example, when four phase shifts are applied (4-bucket algorithm), the height h may be obtained as follows. In Expression 2, zero radian is applied as δ1 to obtain I1, and then Expression 2 is expressed as following Expression 8.

$$I_1 = D\left[1 + \gamma \cos\left(\frac{2\pi h}{\Lambda}\right)\right] \qquad \text{Expression 8}$$

In Expression 2, π/2 radian is applied as δ2 to obtain I2, and then Expression 2 is expressed as following Expression 9.

$$I_2 = D\left[1 + \gamma \cos\left(\frac{2\pi h}{\Lambda} + \frac{\pi}{2}\right)\right] = D\left[1 - \gamma \sin\left(\frac{2\pi h}{\Lambda}\right)\right] \qquad \text{Expression 9}$$

In Expression 2, π radian is applied as δ3 to obtain I3, and then Expression 2 is expressed as following Expression 10.

$$I_3 = D\left[1 + \gamma \cos\left(\frac{2\pi h}{\Lambda} + \pi\right)\right] = D\left[1 - \gamma \cos\left(\frac{2\pi h}{\Lambda}\right)\right] \qquad \text{Expression 10}$$

In Expression 2, 3π/2 radian is applied as δ4 to obtain I4, and then Expression 2 is expressed as following Expression 11.

$$I_4 = D\left[1 + \gamma \cos\left(\frac{2\pi h}{\Lambda} + \frac{3\pi}{2}\right)\right] = D\left[1 + \gamma \sin\left(\frac{2\pi h}{\Lambda}\right)\right] \qquad \text{Expression 11}$$

By using Expression 8, Expression 9, Expression 10 and Expression 11, following Expression 12 is obtained.

$$\frac{I_4 - I_2}{I_1 - I_3} = \tan\left(\frac{2\pi h}{\Lambda}\right) \qquad \text{Expression 12}$$

By using Expression 12, the height h may be obtained as following Expression 13.

$$h = \frac{\Lambda}{2\pi} \tan^{-1}\left[\frac{(I_4 - I_2)}{(I_1 - I_3)}\right] \qquad \text{Expression 13}$$

When grating image is radiated onto the measurement target and captured the reflected image while shifting the grading, three-dimensional shape of the measurement target may be obtained by using Expression 7 or Expression 13.

Figure 5:
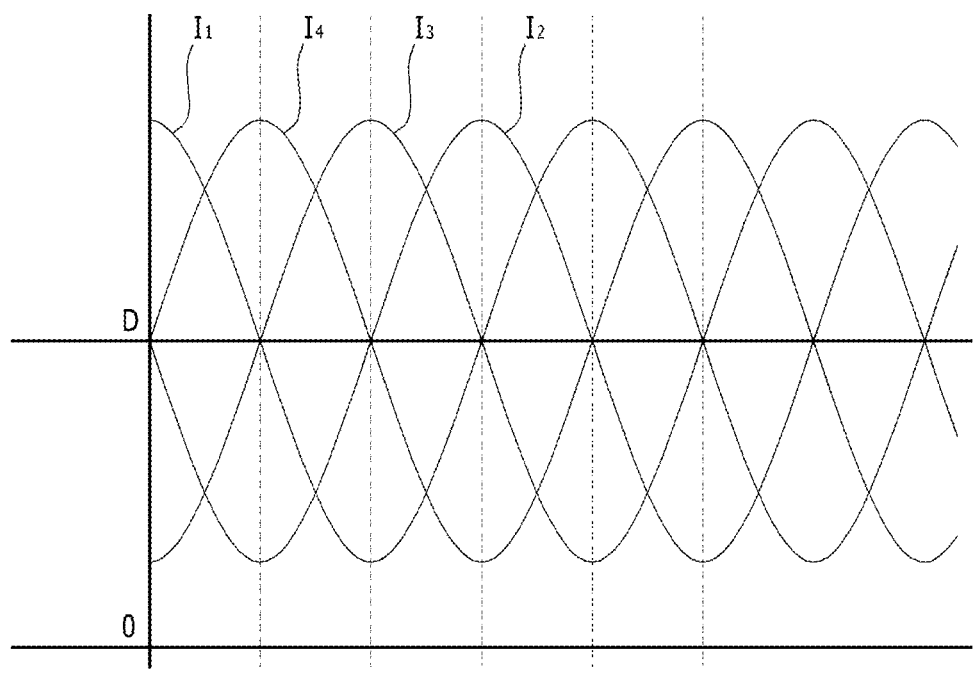
FIG. 5 is graphs showing a principle for measuring a two-dimensional image.

FIG. 5 is graphs showing a principle for measuring a two-dimensional image.

Arithmetic mean value Iave of I1 I2, I3 and I4 may be obtained as following Expression 14.

$$I_{ave} = \frac{I_1 + I_2 + I_3 + I_4}{4} = D \qquad \text{Expression 14}$$

As shown in Expression 14, effect of grating may be offset when averaged, so that two-dimensional shape image may be obtained.

In case of 3-bucket algorithm, arithmetic mean value Iave of I1 I2 and I3 in Expressions 3, 4 and 5, respectively may be expressed as following Expression 15.

$$I_{ave} = \frac{I_1 + I_2 + I_3}{3} = D \qquad \text{Expression 15}$$

On the other hand, the visibility γ in Expression 2 may be expressed as following Expression 16 by using Expression 3, 4, 5 and 15 in case of 3-bucket algorithm.

$$\gamma = \frac{\sqrt{(2I_1 - I_2 - I_3)^2 + 3(I_2 - I_3)^2}}{(I_1 + I_2 + I_3)} \qquad \text{Expression 16}$$

The visibility γ in Expression 2 may be expressed as following Expression 17 by using Expression 8, 9, 10, 11 and 14 in case of 4-bucket algorithm.

$$\gamma = 2\frac{\sqrt{(I_1 - I_3)^2 + (I_2 - I_4)^2}}{(I_1 + I_2 + I_3 + I_4)} \qquad \text{Expression 17}$$

According to the present invention, two-dimensional shape image may be obtained by using three-dimensional data measured, so that additional data for two-dimensional shape image may be not required.

Furthermore, when two-dimensional shape image and three-dimensional shape image, both of which are measured, are used together, defects of PCB may be effectively inspected.

Figure 6:
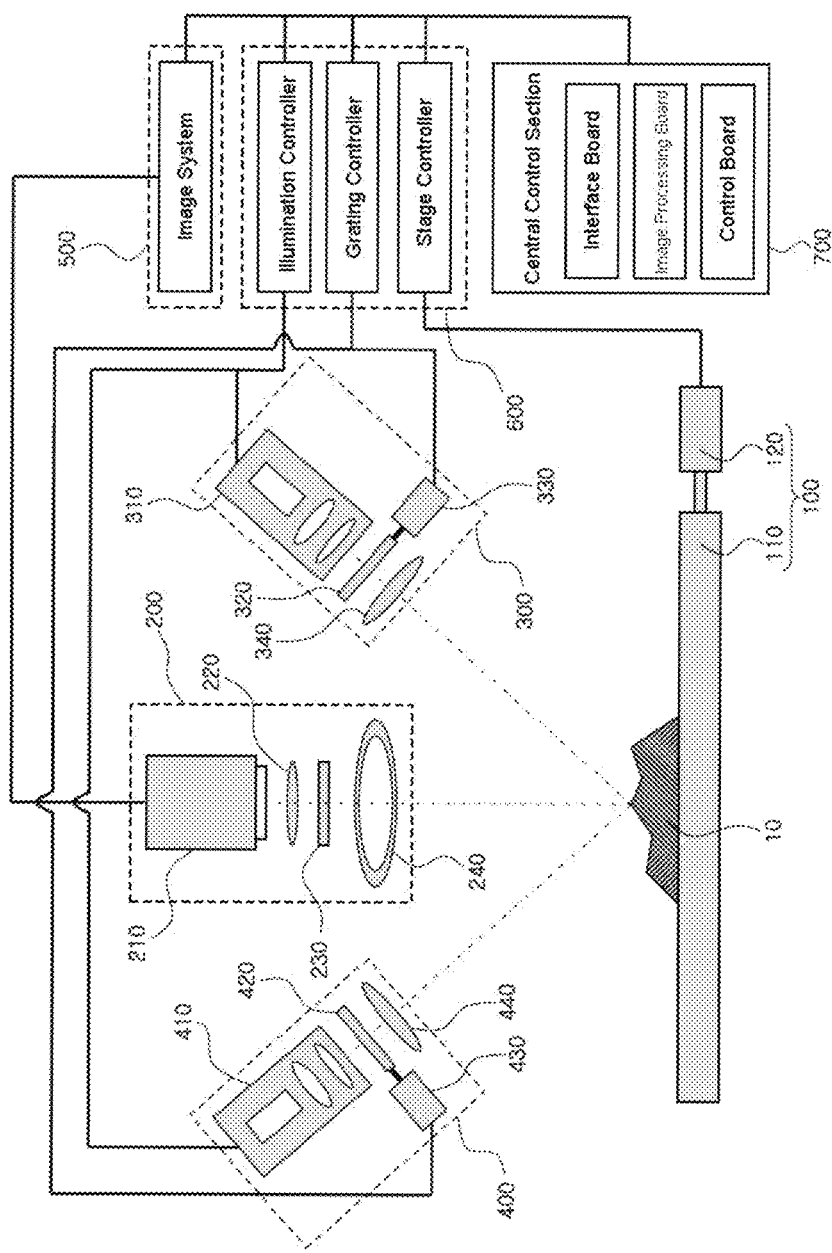
FIG. 6 is a schematic view illustrating a three dimensional shape measurement apparatus used to a method of measuring a three dimensional shape according to an exemplary embodiment of the present invention.

FIG. 6 is a schematic view illustrating a three dimensional shape measurement apparatus used to a method of measuring a three dimensional shape according to an exemplary embodiment of the present invention.

Referring to FIG. 6, a three dimensional shape measurement apparatus used to a method of measuring a three dimensional shape according to an exemplary embodiment of the present invention may include a measurement stage section 100, an image photographing section 200, first and second illumination sections 300 and 400, an image acquiring section 500, a module control section 600 and a central control section 700.

The measurement stage section 100 may include a stage 110 supporting a measurement target 10 and a stage transfer unit 120 transferring the stage 110. In an exemplary embodiment, according as the measurement target 10 moves with respect to the image photographing section 200 and the first and second illumination sections 300 and 400 by the stage 110, a measurement location may be changed in the measurement target 10.

The image photographing section 200 is disposed over the stage 110 to receive light reflected by the measurement target 10 and measure an image of the measurement target 10. That is, the image photographing section 200 receives the light that exits the first and second illumination sections 300 and 400 and is reflected by the measurement target 10, and photographs a plan image of the measurement target 10.

The image photographing section 200 may include a camera 210, an imaging lens 220, a filter 230 and a lamp 240. The camera 210 receives the light reflected by the measurement target 10 and photographs the plan image of the measurement target 10. The camera 210 may include, for example, one of a CCD camera and a CMOS camera. The imaging lens 220 is disposed under the camera 210 to image the light reflected by the measurement target 10 on the camera 210. The filter 230 is disposed under the imaging lens 220 to filter the light reflected by the measurement target 10 and provide the filtered light to the imaging lens 220. The filter 230 may include, for example, one of a frequency filter, a color filter and a light intensity control filter. The lamp 240 may be disposed under the filter 230 in a circular shape to provide the light to the measurement target 10, so as to photograph a particular image such as a two-dimensional shape of the measurement target 10.

The first illumination section 300 may be disposed, for example, at a right side of the image photographing section 200 to be inclined with respect to the stage 110 supporting the measurement target 10. The first illumination section 300 may include a first light source unit 310, a first grating unit 320, a first grating transfer unit 330 and a first condensing lens 340. The first light source unit 310 may include a light source and at least one lens to generate light, and the first grating unit 320 is disposed under the first light source unit 310 to change the light generated by the first light source unit 310 into a first grating pattern light having a grating pattern. The first grating transfer unit 330 is connected to the first grating unit 320 to transfer the first grating unit 320, and may include, for example, one of a piezoelectric transfer unit and a fine linear transfer unit. The first condensing lens 340 is disposed under the first grating unit 320 to condense the first grating pattern light exiting the first grating unit 320 on the measurement target 10.

For example, the second illumination section 400 may be disposed at a left side of the image photographing section 200 to be inclined with respect to the stage 110 supporting the measurement target 10. The second illumination section 400 may include a second light source unit 410, a second grating unit 420, a second grating transfer unit 430 and a second condensing lens 440. The second illumination section 400 is substantially the same as the first illumination section 300 described above, and thus any further description will be omitted.

When the first grating transfer unit 330 sequentially moves the first grating unit 320 by N times and N first grating pattern lights are illuminated onto the measurement target 10 in the first illumination section 300, the image photographing section 200 may sequentially receive the N first grating pattern lights reflected by the measurement target 10 and photograph N first pattern images. In addition, when the second grating transfer unit 430 sequentially moves the second grating unit 420 by N times and N first grating pattern lights are illuminated onto the measurement target 10 in the second illumination section 400, the image photographing section 200 may sequentially receive the N second grating pattern lights reflected by the measurement target 10 and photograph N second pattern images. The 'N' is a natural number, and for example may be four.

In an exemplary embodiment, the first and second illumination sections 300 and 400 are described as an illumination apparatus generating the first and second grating pattern lights. Alternatively, the illumination section may be more than or equal to three. In other words, the grating pattern light may be illuminated onto the measurement target 10 in various directions, and various pattern images may be photographed. For example, when three illumination sections are disposed in an equilateral triangle form with the image photographing section 200 being the center of the equilateral triangle form, three grating pattern lights may be illuminated onto the measurement target 10 in different directions. For example, when four illumination sections are disposed in a square form with the image photographing section 200 being the center of the square form, four grating pattern lights may be illuminated onto the measurement target 10 in different directions.

The image acquiring section 500 is electrically connected to the camera 210 of the image photographing section 200 to acquire the pattern images from the camera 210 and store the acquired pattern images. For example, the image acquiring section 500 may include an image system that receives the N first pattern images and the N second pattern images photographed in the camera 210 and stores the images.

The module control section 600 is electrically connected to the measurement stage section 100, the image photographing section 200, the first illumination section 300 and the second illumination section 400, to control the measurement stage section 100, the image photographing section 200, the first illumination section 300 and the second illumination section 400. The module control section 600 may include, for example, an illumination controller, a grating controller and a stage controller. The illumination controller controls the first and second light source units 310 and 410 to generate light, and the grating controller controls the first and second grating transfer units 330 and 430 to move the first and second grating units 320 and 420. The stage controller controls the stage transfer unit 120 to move the stage 110 in an up-and-down motion and a left-and-right motion.

The central control section 700 is electrically connected to the image acquiring section 500 and the module control section 600 to control the image acquiring section 500 and the module control section 600. Particularly, the central control section 700 receives the N first pattern images and the N second pattern images from the image system of the image acquiring section 500 to process the images, so that three dimensional shape of the measurement target may be measured. In addition, the central control section 700 may control an illumination controller, a grating controller and a stage controller of the module control section 600. Thus, the central control section may include an image processing board, a control board and an interface board.

Hereinafter, a method of measuring the measurement target 10 formed on a printed circuit board by using the above described three dimensional shape measurement apparatus will be described in detail. It will be described employing a solder as an example of the measurement target 10.

Figure 7:
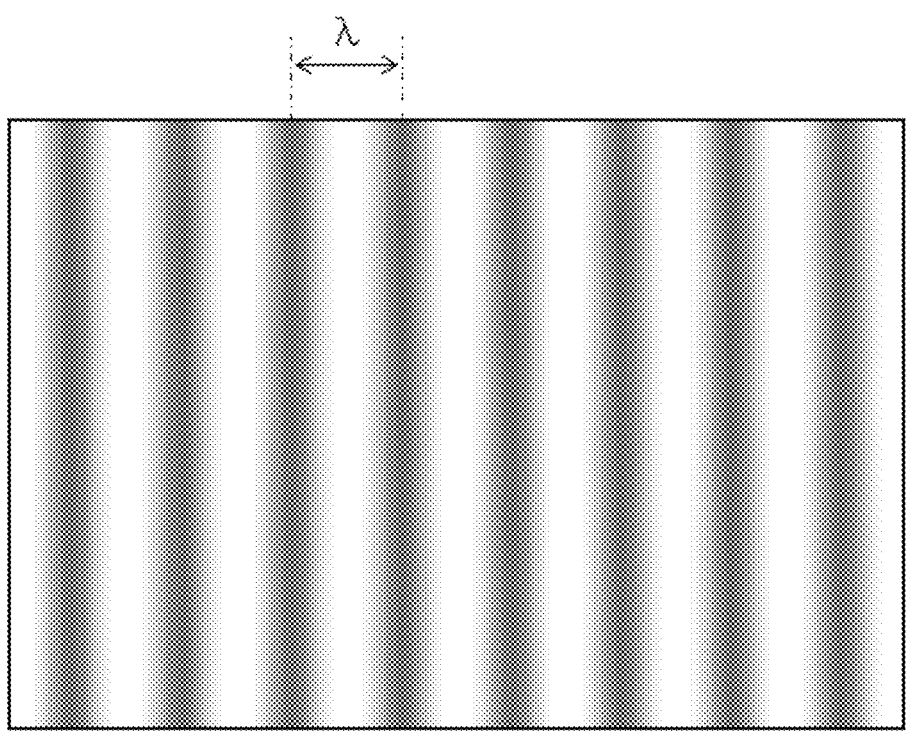
FIG. 7 is a plan view illustrating a grating pattern image by a grating pattern light illuminated onto a measurement target in FIG. 6.

FIG. 7 is a plan view illustrating a grating pattern image by a grating pattern light illuminated onto a measurement target in FIG. 6.

Referring to FIGS. 6 and 7, when the grating pattern light from one of the plurality of the illumination sections is illuminated onto the measurement target 10, a grating pattern image is formed on the measurement target 10. The grating pattern image includes a plurality of grating patterns, and in the present embodiment, an interval between the grating patterns, i.e., a grating pitch is defined as a measurement scope $\lambda$.

The measurement scope $\lambda$ may be the same irrespective of sorts of the grating pattern lights, but alternatively, may be different from each other according to sorts of the grating pattern lights. The measurement scope $\lambda$ may have at least two values according to sorts of the grating pattern lights. For example, the grating pattern image by the first grating pattern light generated from the first illumination section 300 may have grating patterns of a first measurement scope, and the grating pattern image by the second grating pattern light generated from the second illumination section 400 may have grating patterns of a second measurement scope different from the first measurement scope.

Figure 8:
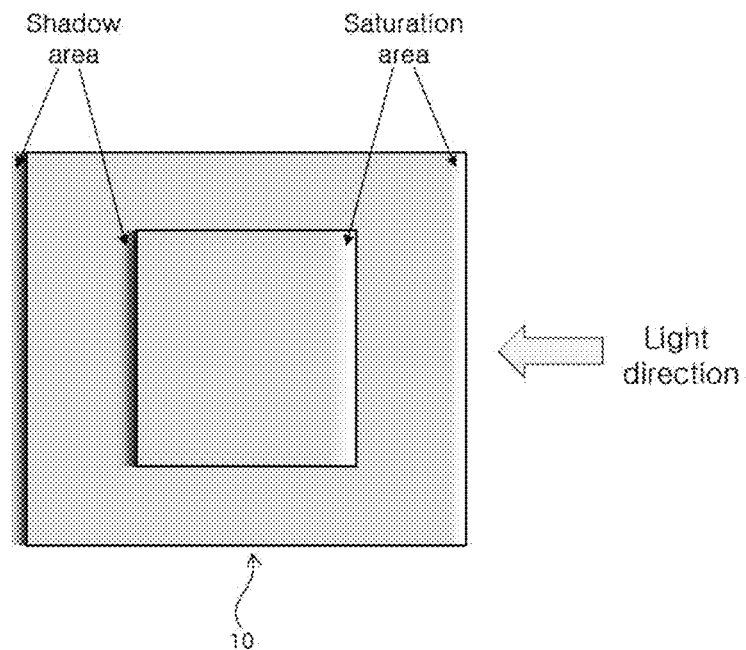
FIG. 8 is a plan view illustrating an image measured in the camera when the grating pattern light is illuminated onto the measurement target from a right side.
Figure 9:
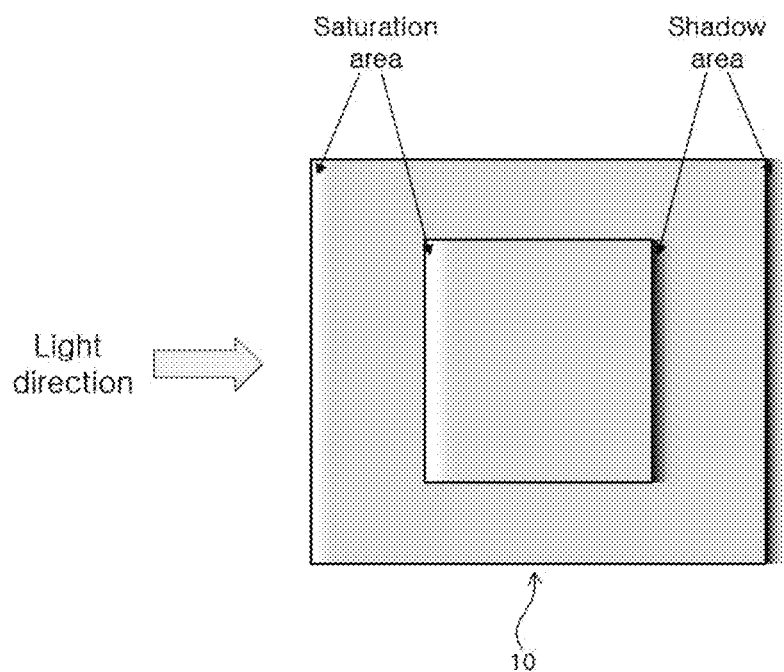
FIG. 9 is a plan view illustrating an image measured in the camera when the grating pattern light is illuminated onto the measurement target from a left side.

FIG. 8 is a plan view illustrating an image measured in the camera when the grating pattern light is illuminated onto the measurement target from a right side. FIG. 9 is a plan view illustrating an image measured in the camera when the grating pattern light is illuminated onto the measurement target from a left side. In the images of FIGS. 8 and 9, a relative amount with respect to brightness (luminance) is just shown, and the grating pattern is omitted.

Referring to FIGS. 6, 8 and 9, when the grating pattern light from one of the plurality of the illumination sections is illuminated onto the measurement target 10, an image photographed in the camera 210 may include a shadow area that is relatively dark and a saturation area that is relatively bright.

For example, as shown in FIG. 8, when the grating pattern light is illuminated onto the measurement target 10 from right side, typically, the saturation area is formed at a right portion of the measurement target 10, and the shadow area is formed at a left portion of the measurement target 10. In contrast, as shown in FIG. 9, when the grating pattern light is illuminated onto the measurement target 10 from left side, typically, the saturation area is formed at a left portion of the measurement target 10, and the shadow area is formed at a right portion of the measurement target 10.

Hereinafter, referring again to FIGS. 6 to 8, a method of measuring a three dimensional shape according to the present embodiment will be described based on the above described explanation.

Firstly, the grating pattern lights generated in a plurality of directions are sequentially illuminated onto the measurement target 10 disposed on the stage 110, and the grating pattern lights reflected by the measurement target 10 are sequentially detected in the camera 210 to acquire a plurality of pattern images.

Particularly, each of the grating pattern lights is moved aside and illuminated onto the measurement target 10 by N times, for example, three times or four times, to acquire N pattern images of the measurement target 10 for each of the directions. For example, as shown in FIG. 6, when the first and second grating pattern lights generated from the first and second illumination sections 300 and 400 are illuminated onto the measurement target 10, N first pattern images and N second pattern images may be acquired.

Then, N brightness degrees $\{I^i_1, I^i_2, \ldots, I^i_N\}$ at each position $\{i(x,y)\}$ in an X-Y coordinate system, and the measurement scope $\lambda$ as shown in FIG. 7 are extracted from N pattern images with respect to each direction. Thereafter, phase $\{P_i(x,y)\}$, brightness $\{A_i(x,y)\}$ and visibility $\{V_i(x,y)\}$ with respect to each direction are calculated from the N brightness degrees $\{I^i_1, I^i_2, \ldots, I^i_N\}$. The phase $\{P_i(x,y)\}$, the brightness $\{A_i(x,y)\}$ and the visibility $\{V_i(x,y)\}$ with respect to each direction may be calculated by using an N-bucket algorithm. In addition, the brightness $\{A_i(x,y)\}$ may be an average brightness that is obtained by averaging the detected grating pattern lights. Thus, hereinafter, the brightness $\{A_i(x,y)\}$ will be called "average brightness $\{A_i(x,y)\}$".

For example, when N is 3, three brightness degrees $\{I^i_1, I^i_2, I^i_3\}$ are extracted from three pattern images with respect to each direction, and phase $\{P_i(x,y)\}$, average brightness $\{A_i(x,y)\}$ and visibility $\{V_i(x,y)\}$ may be calculated as shown in the following equations through a three-bucket algorithm. In the following equations, $B_i(x,y)$ indicates an amplitude of an image signal (brightness signal) in three pattern images with respect to each direction. $I^i_1$ corresponds to "a+b cos($\Phi$)", $I^i_2$ corresponds to "a+b cos($\phi$+2$\pi$/3)", and $I^i_3$ corresponds to "a+b cos($\phi$+4$\pi$/3)".

$$P_i(x,y) = \tan^{-1} \frac{\sqrt{3}(I^i_3 - I^i_2)}{2I^i_1 - I^i_2 - I^i_3}$$

$$A_i(x,y) = \frac{I^i_1 + I^i_2 + I^i_3}{3}$$

$$V_i(x,y) = \frac{B_i}{A_i} = \frac{\sqrt{(2I^i_1 - I^i_2 - I^i_3)^2 + 3(I^i_2 - I^i_3)^2}}{(I^i_1 + I^i_2 + I^i_3)}$$

In contrast, for example, when N is 4, four brightness degrees $\{I^i_1, I^i_2, I^i_3, I^i_4\}$ are extracted from four pattern images with respect to each direction, and phase $\{P_i(x,y)\}$, average brightness $\{A_i(x,y)\}$ and visibility $\{V_i(x,y)\}$ may be calculated as shown in the following equations through a four-bucket algorithm. In the following equations, $B_i(x,y)$ indicates an amplitude of an image signal (brightness signal) in four pattern images with respect to each direction. $I^i_1$ corresponds to "a+b cos($\Phi$)", $I^i_2$ corresponds to "a+b cos($\phi$+$\pi$/2)", and $I^i_3$ corresponds to "a+b cos($\phi$+$\pi$)" and $I^i_4$ corresponds to "a+b cos(p+3$\pi$/2)".

$$P_i(x,y) = \tan^{-1} \frac{I^i_4 - I^i_2}{I^i_1 - I^i_3}$$

$$A_i(x,y) = \frac{I^i_1 + I^i_2 + I^i_3 + I^i_4}{4}$$

$$V_i(x,y) = \frac{B_i}{A_i} = \frac{2\sqrt{(I^i_1 - I^i_3)^2 + (I^i_2 - I^i_4)^2}}{(I^i_1 + I^i_2 + I^i_3 + I^i_4)}$$

In an exemplary embodiment, a signal-to-noise ratio (SNR) may be calculated and used in place of the visibility $\{V_i(x,y)\}$ or together with the visibility $\{V_i(x,y)\}$. The SNR Indicates a ratio of an image signal S to a noise signal N (S/N) in N pattern images with respect to each direction.

Thereafter, height $\{H_i(x,y)\}$ with respect to each direction is calculated from the phase $\{P_i(x,y)\}$ with respect to each direction by the following equation. In the following equation, $k_i(x,y)$ is a phase-to-height conversion scale that indicates a conversion ratio between a phase and a height.

$$H_i(x,y) = k_i(x,y) \cdot P_i(x,y)$$

Height weight $\{W_i(x,y)\}$ with respect to each direction is calculated by using at least one of the average brightness $\{A_i(x,y)\}$, the visibility $\{V_i(x,y)\}$ and the measurement scope $\lambda$. The height weight $\{W_i(x,y)\}$ with respect to each direction may be obtained as follows by a weight function $\{f(A_i,V_i,\lambda)\}$ having parameters of, for example, the average brightness $\{A_i(x,y)\}$, the visibility $\{V_i(x,y)\}$ and the measurement scope ($\lambda$). Sum of the height weights in the total directions may be 1 $\{\Sigma W_i(x,y)=1\}$.

$$W_i(x,y) = f(A_i, V_i, \lambda)$$

Then, the height $\{H_i(x,y)\}$ with respect to each direction is multiplied by the height weight $\{W_i(x,y)\}$ with respect to each direction to calculate weight height $\{W_i(x,y) \cdot H_i(x,y)\}$ with respect to each direction. Thereafter, the weight heights in the total directions are summed and divided by the sum of the height weights $\{\Sigma W_i(x,y)\}$ to calculate height $\{\Sigma W_i(x,y) \cdot H_i(x,y)/\Sigma W_i(x,y)\}$ at each position.

Then, the three dimensional shape of the measurement target 10 may be accurately measured by combining the heights according to positions calculated as the above.

Hereinafter, relations between the height weight $\{W_i(x,y)\}$ with respect to each direction and characteristics of the weight function $\{f(A_i,V_i,\lambda)\}$, i.e., the average brightness $\{A_i(x,y)\}$, the visibility $\{V_i(x,y)\}$ or the SNR, and the measurement scope $\lambda$, will be described in detail.

Figure 10:
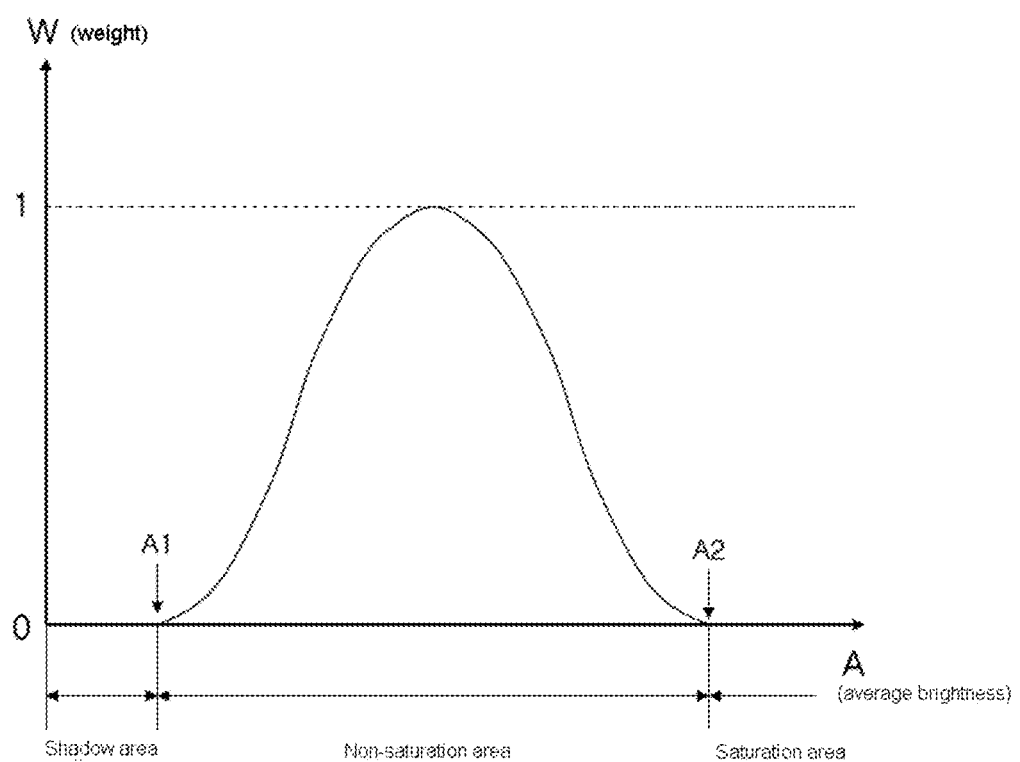
FIG. 10 is a graph showing a relation between average brightness and weight of the pattern images measured in the camera.

FIG. 10 is a graph showing a relation between average brightness and weight of the pattern images measured in the camera.

Referring to FIG. 10, firstly, when the average brightness $\{A_i(x,y)\}$ increases or decreases from a predetermined value that is set in advance, the weight function $\{f(A_i,V_i,\lambda)\}$ may act on the height weight $\{W_i(x,y)\}$ to decrease. In other words, when the average brightness $\{A_i(x,y)\}$ has the predetermined value, the height weight $\{W_i(x,y)\}$ has relatively the greatest value, and as the average brightness $\{A_i(x,y)\}$ becomes distant from the predetermined value, the height weight $\{W_i(x,y)\}$ may decrease. The predetermined value may be set when determining a three dimensional condition by using a specimen stone or may be arbitrarily set by a user. However, the predetermined value may preferably be an average value, i.e., a mid value of the average brightness $\{A_i(x,y)\}$.

Figure 11:
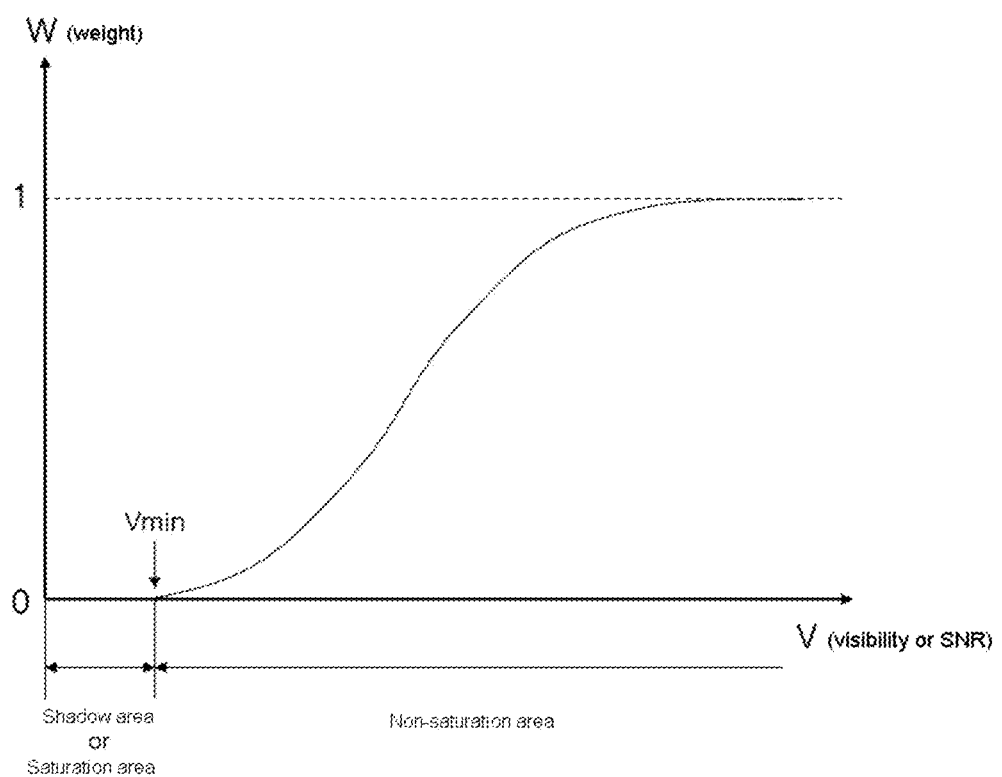
FIG. 11 is a graph showing a relation between visibility or SNR and weight of the pattern images measured in the camera.

FIG. 11 is a graph showing a relation between visibility or SNR and weight of the pattern images measured in the camera.

Referring to FIG. 11, thereafter, when the visibility $\{V_i(x,y)\}$ or the SNR increases, the weight function $\{f(A_i,V_i,\lambda)\}$ may act on the height weight to increase. In other words, as the visibility $\{V_i(x,y)\}$ or the SNR slowly increases, the height weight $\{W_i(x,y)\}$ may also slowly increase.

Figure 12:
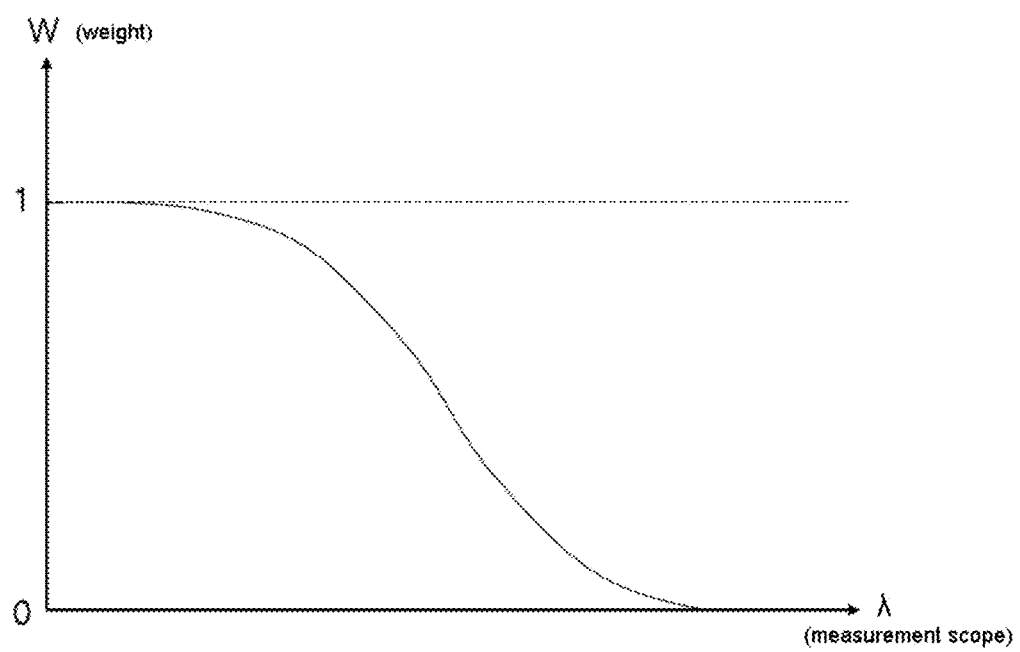
FIG. 12 is a graph showing a relation between measurement scope and weight of the pattern images measured in the camera.

FIG. 12 is a graph showing a relation between measurement scope and weight of the pattern images measured in the camera.

Referring to FIG. 12, then, when the measurement scope $\lambda$ increases, the weight function $\{f(A_i,V_i,\lambda)\}$ may act on the height weight $\{W_i(x,y)\}$ to decrease. In other words, as the measurement scope $\lambda$ slowly increases, the height weight $\{W_i(x,y)\}$ may slowly decrease.

Referring again to FIGS. 7, 10 and 11, the N pattern images with respect to each direction are divided into a shadow area, a saturation area and non-saturation area, and different height weight $\{W_i(x,y)\}$ may be given according to each area. In the shadow area, the average brightness $\{A_i(x,y)\}$ is below a minimum brightness A1, and the visibility $\{V_i(x,y)\}$ or the SNR is below a minimum reference value Vmin. In the saturation area, the average brightness $\{A_i(x,y)\}$ is more than a maximum brightness A2, and the visibility or the SNR is below the minimum reference value Vmin. The non-saturation area corresponds to a remaining area except the shadow area and the saturation area.

Firstly, in the shadow area and the saturation area, the weight function $\{f(A_i,V_i,\lambda)\}$ is regarded as '0' to obtain the height weight $\{W_i(x,y)\}$. In other words, in the shadow area and the saturation area, the height weight $\{W_i(x,y)\}$ is determined as '0'.

Then, in the non-saturation area, as shown in FIGS. 10 to 12, the weight function $\{f(A_i,V_i,\lambda)\}$ may decrease the height weight $\{W_i(x,y)\}$ when the average brightness $\{A_i(x,y)\}$ increases or decreases from the mid value, increase the height weight $\{W_i(x,y)\}$ when the visibility $\{V_i(x,y)\}$ or the SNR increases, and decrease the height weight $\{W_i(x,y)\}$ when the measurement scope $\lambda$ increases.

In contrast, in the non-saturation area, the weight function $\{f(A_i,V_i,\lambda)\}$ may be regarded as the same to obtain the height weight $\{W_i(x,y)\}$. For example, when height weights with respect to four directions in the non-saturation area are called for first, second, third and fourth height weights $W_1$, $W_2$, $W_3$ and $W_4$, all of the first, second, third and fourth height weights $W_1$, $W_2$, $W_3$ and $W_4$ may be determined as '¼'.

According to the present embodiment, the average brightness $\{A_i(x,y)\}$, the visibility $\{V_i(x,y)\}$ or SNR, and the measurement scope $\lambda$ are extracted from the N pattern images photographed in each directions, and the height weight $\{W_i(x,y)\}$ is determined according to the extraction result, thereby accurately measuring the height according to each position of the measurement target 10 in all the areas.

Especially, the N pattern images with respect to each direction are divided into the shadow area, the saturation area and the non-saturation area, and different height weight $\{W_i(x,y)\}$ is given according to each area, to thereby prevent reliability reduction for the height in the shadow area and the saturation area. In other words, the height weight $\{W_i(x,y)\}$ is given as relatively low value, for example, '0' in the shadow area and the saturation area, the height weight $\{W_i(x,y)\}$ is given as relatively great value in the non-saturation area, thereby compensating for adverse effect incurred from the shadow area and the saturation area to more accurately measure a three dimensional shape of the measurement target.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A method of measuring a three dimensional shape comprising:
   illuminating grating pattern lights in a plurality of directions onto a measurement target by N times and acquiring N pattern images reflected from the measurement target with respect to each direction, wherein a plurality of pattern-projecting sections disposed in the plurality of directions illuminates the grating pattern lights in the plurality of directions;
   extracting a phase with respect to each direction, corresponding to each position from the N pattern images;
   extracting N brightness degrees from the N pattern images with respect to each direction, corresponding to each position:
   averaging the N brightness degrees with respect to each direction to obtain an average brightness with respect to each direction, corresponding to each position;
   extracting a height weight with respect to each direction by using a weight function employing the average brightness as a parameter;
   calculating a weight height with respect to each direction by using a height based on the phase and the height weight; and
   calculating a height at each position by using weight heights with respect to the plurality of directions associated with the plurality of pattern-projecting sections.

2. The method of claim 1, wherein the grating pattern lights illuminated by N times includes pattern lights each having different patterns.

3. The method of claim 1, further comprising measuring a three dimensional shape by combining the height at each position.

4. The method of claim 1, wherein sum of the height weights with respect to the plurality of directions is equal to 1.

5. The method of claim 1, wherein the weight function further employs at least one of a visibility and a signal-to-noise ratio (SNR) with respect to each direction extracted from the pattern images with respect to each direction as parameters.

6. The method of claim 5, wherein the weight function further employs a measurement scope ($\lambda$) corresponding to a grating pitch of each grating pattern light extracted from the pattern images with respect to each direction as a parameter.

7. The method of claim 6, wherein the measurement scope has at least two values according to the grating pattern lights.

8. The method of claim 6, wherein the weight function decreases the height weight, as the measurement scope increases.

9. The method of claim 5, wherein
the weight function decreases the height weight, as the average brightness increases or decreases from a predetermined value.

10. The method of claim 9, wherein the predetermined value is a mid value of the average brightness.

11. The method of claim 5, wherein the weight function increases the height weight, as the visibility or the SNR increases.

12. The method of claim 5,
wherein extracting the height weight with respect to each direction comprising dividing the pattern images into a shadow area, a saturation area and a non-saturation area, and
wherein the shadow area corresponds to an area, in which the average brightness is below a minimum brightness and the visibility or the SNR is below a minimum reference value,
the saturation area corresponds to an area, in which the average brightness is more than a maximum brightness and the visibility or the SNR is below the minimum reference value, and
the non-saturation area corresponds to a remaining area except the shadow area and the saturation area.

13. The method of claim 12, wherein the weight function is calculated by regarding the height weight as '0' in the shadow area and the saturation area.

14. The method of claim 13, wherein the weight function corresponding to the non-saturation area decreases the height weight, as the average brightness increases or decreases from a mid value of the average brightness, and increases the height weight as the visibility or the SNR increases.

15. A method of measuring a three dimensional shape comprising:
illuminating grating pattern lights in a plurality of directions onto a measurement target by N times and acquiring N pattern images of the measurement target with respect to each direction, wherein a plurality of pattern-projecting sections disposed in the plurality of directions illuminates the grating pattern lights in the plurality of directions;
extracting a phase and a visibility with respect to each direction, corresponding to each position from the N pattern images;
extracting a height weight with respect to each direction by using a weight function employing the visibility as a parameter;
calculating a weight height with respect to each direction by using a height based on the phase and the height weight; and
calculating a height at each position by using weight heights with respect to the plurality of directions associated with the plurality of pattern-projecting sections,
wherein the visibility is an amplitude of brightness signal divided by an average brightness.

16. The method of claim 15, further comprising measuring a three dimensional shape by combining the height at each position.

17. The method of claim 15, wherein sum of the height weights with respect to the plurality of directions is equal to 1.

* * * * *